United States Patent [19]
Schickling et al.

[11] Patent Number: 4,820,283
[45] Date of Patent: Apr. 11, 1989

[54] SHEAR FORCE GAUGE

[75] Inventors: David P. Schickling, Orange; Patrick M. Maloney, El Toro, both of Calif.

[73] Assignee: Baxter Travenol Laboratories, Inc., Deerfield, Ill.

[21] Appl. No.: 143,738

[22] Filed: Jan. 13, 1988

[51] Int. Cl.[4] .............................................. A61M 25/00
[52] U.S. Cl. .................................... 604/280; 128/774; 73/862.39
[58] Field of Search ...................... 604/280, 95, 93, 96, 604/97, 100; 128/774; 73/862.39, 862.62

[56] References Cited

U.S. PATENT DOCUMENTS

| | | | |
|---|---|---|---|
| 42,801 | 5/1864 | Sleppy | 73/862.42 |
| 326,067 | 9/1885 | Sturtevant | 73/862.39 |
| 3,693,418 | 9/1972 | Kaspareck . | |
| 4,351,341 | 9/1982 | Goldberg et al. . | |
| 4,370,982 | 2/1983 | Reilly . | |
| 4,614,188 | 9/1986 | Bazell et al. . | |
| 4,721,507 | 1/1988 | Chin | 128/774 |

*Primary Examiner*—Stephen C. Pellegrino
*Attorney, Agent, or Firm*—Loyal M. Hanson; Gordon L. Peterson

[57] ABSTRACT

A device for use in withdrawing a catheter such as a balloon catheter from a vessel in the vascular system in order to inhibit damage to the vessel wall includes an assembly defining a passageway through which to pass the catheter. The assembly is dimensioned and arranged to be grasped by a user, and it includes components for coupling the assembly to the catheter so that the user can withdraw the catheter from the vessel by moving the assembly generally axially. The coupling components are adjustable to enable the user to select a desired maximum amount of force that can be coupled from the assembly to the catheter, and for this purpose one embodiment includes a cap-and-compressible-disk arrangement on a body member in which a spring-coupled handle member is telescopingly disposed, graduations along the handle member providing a visually discernible indication of relative handle member position and therefore of the magnitude of a force being coupled by the user to the assembly.

18 Claims, 2 Drawing Sheets

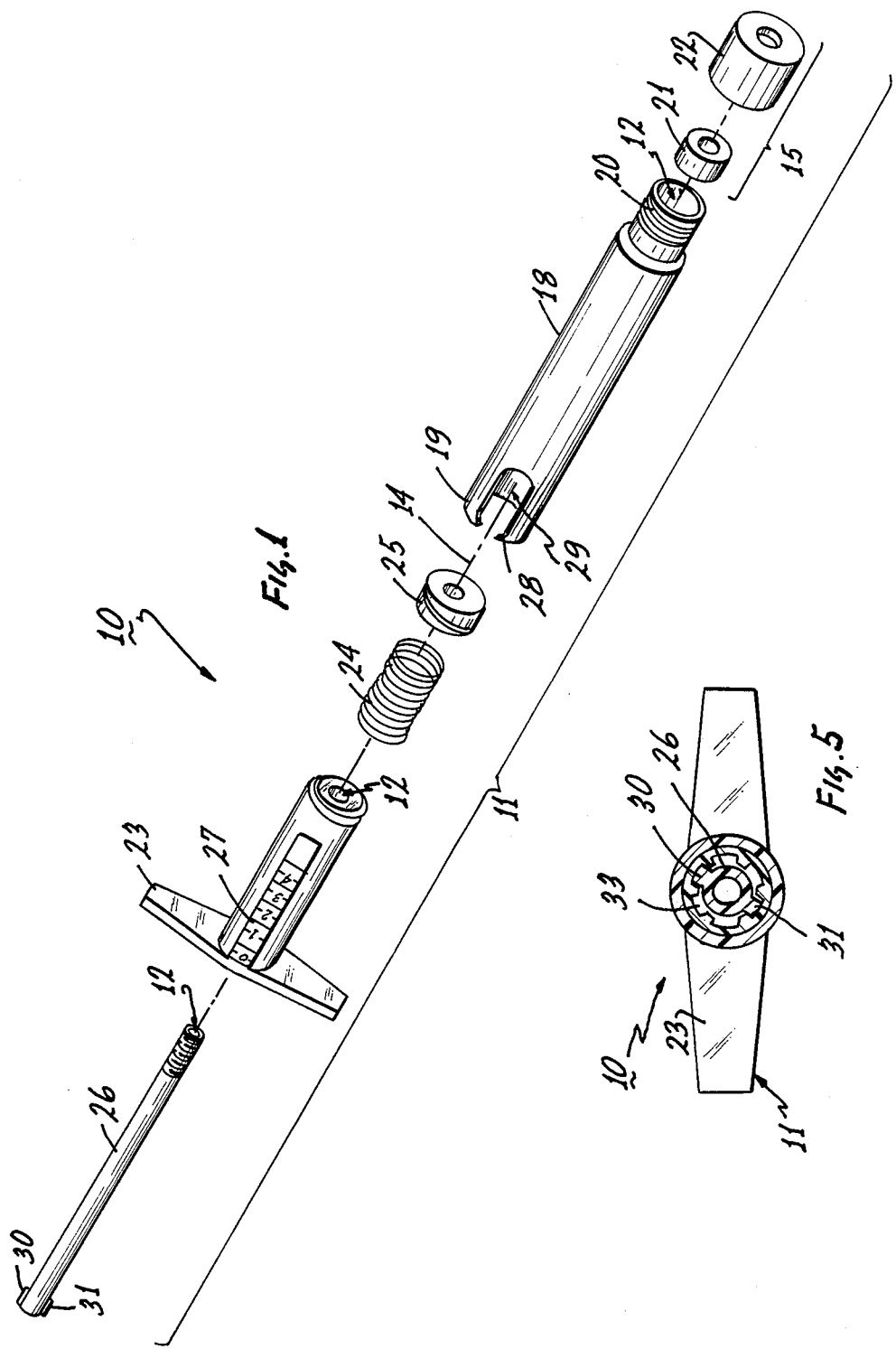

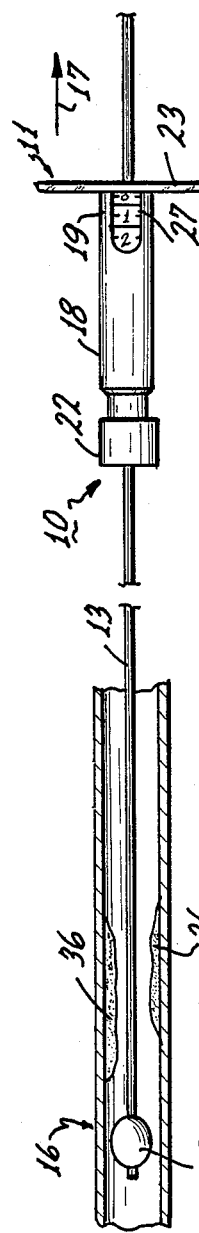
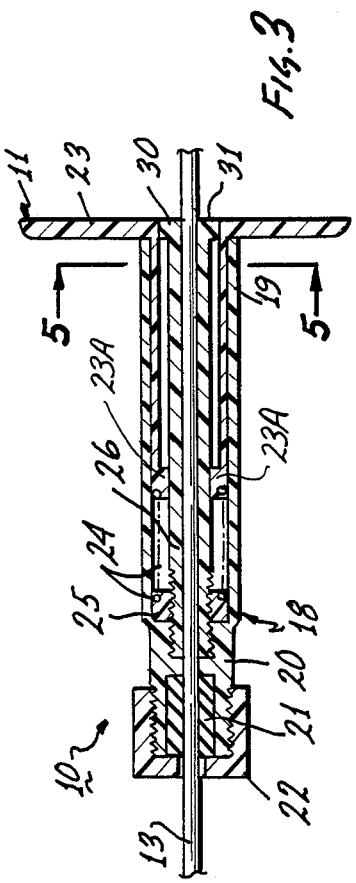
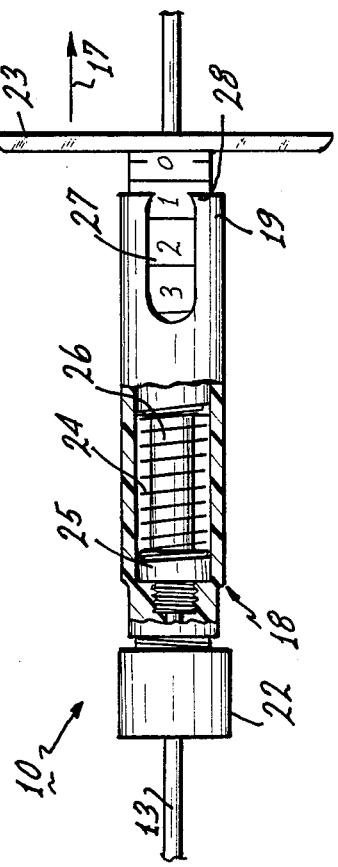

SHEAR FORCE GAUGE

BACKGROUND OF THE INVENTION

1. Technical Field

This invention relates generally to catheters that are inserted into the vascular system, and more particularly to a device for inhibiting damage to a vessel from shear forces produced as the catheter is withdrawn.

2. Background Information

As a catheter is withdrawn from a vessel, it can exert shear forces that may damage the vessel wall. This concern is common to catheters used for dilation purposes during internal mammary artery bypass procedure, as well as those used for embolectomy and thrombectomy purposes. Use of a balloon embolectomy catheter, for example, includes movement of a balloon located on the distal end of the catheter through an area of arterial obstruction (caused, for example, by an embolism or thrombosis) until the balloon has passed the obstruction. Then, the pliable embolectomy balloon is inflated, trapping the obstructing material proximal to the balloon, and the catheter is withdrawn to remove the obstruction.

The degree of balloon inflation is important because overinflation relative to the size of the vessel can result in a large axially-directed or shear force being exerted on the vessel wall by the balloon as the catheter is withdrawn. As shown by electron microscopy studies, this increased shear force can strip cell layers from the arterial endothelium. In addition, high shear forces during embolectomy catheter use may lead to intimal flap formation, with reocclusion of the vessel.

Consequently, it is desirable to have some means of alleviating this concern so that the surgeon can better avoid damage to the vessel wall resulting from shear forces produced during catheter withdrawal.

SUMMARY OF THE INVENTION

This invention solves the problems outlined above by providing a device that can be attached to the proximal end of the catheter for the surgeon to grip when withdrawing the catheter. The device couples only a desired maximum amount of force to the catheter so that vessel wall damage can be prevented. In addition, the device can provide a visually discernible indication of the force being coupled. Thus, the device enables the surgeon to regulate the maximum force applied and to monitor the force as it is applied.

Generally, a shear force gauge apparatus constructed according to the invention includes an assembly defining a passageway through which to thread a catheter. The assembly is dimensioned and arranged to be grasped by a user, and it includes coupling components for coupling the assembly to the catheter so that the user can withdraw the catheter from a vessel by moving the assembly.

According to a major aspect of the invention, the coupling components are adjustable to enable the user to select a desired maximum amount of force that can be coupled from the assembly to the catheter. This is accomplished in one embodiment with a cap-and-compressible-disk arrangement on the assembly of the type sometimes called a Touhy-Borst cap-and-disk arrangement whereby an annular disk of elastomeric material is compressed against the catheter by adjusting a screw-on cap over the disk. Although this type of coupling concept is well known, the invention combines it with components subsequently described for catheter retention to facilitate quick and convenient setting of maximum shear force.

According to another aspect of the invention, there is provided an arrangement for providing a visually discernible indication of the relative magnitude of a force being coupled by the user to the assembly, and, therefore, from the assembly to the catheter. For this purpose, one embodiment includes an axially moveable handle member telescopingly disposed and spring-coupled within a body member that is coupled to the catheter. Handle member position corresponds to the force applied, and a graduated scale disposed on the assembly provides an indication of relative handle member position.

Numerous force gauges exist in the art. However, the gauge of this invention is specially configured for particular medical applications. In addition, the gauge can be made entirely from plastic so that it is disposable and ETO sterilizable, unlike many other existing gauges.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 is an exploded isometric view of a device constructed according to the invention, shown enlarged over its actual size;

FIG. 2 is a diagrammatic representation of the device as it is used in withdrawing a catheter from a vessel;

FIG. 3 is an enlarged elevation view of the device taken in cross section;

FIG. 4 is another enlarged view showing certain aspects of device operation; and FIG. 5 is a cross sectional view of the device taken on line 5—5 of FIG. 3.

DESCRIPTION OF THE PREFERRED EMBODIMENTS

Referring now to the drawings, there is shown a device 10 constructed according to the invention. Generally, the device 10 includes an assembly 11 of components that defines a passageway 12 through which to thread or pass a catheter, such as a catheter 13 as shown in FIGS. 2-4. The passageway 12 has a cross sectional area sufficient to receive the catheter 13 so that the catheter 13 can be threaded through the passageway 12, either just prior to use or as a step in fabricating a catheter (such as a balloon embolectomy catheter) with a preinstalled device 10, for example.

The assembly 11 is dimensioned and arranged to be grasped by a user for purposes of withdrawing the catheter 13 from a vessel, the illustrated embodiment being about seven centimeters long and configured with the passageway 12 extending through each of the components of the assembly 11, along a longitudinal axis 14 of the assembly 11. The assembly 11 includes coupling components 15 (FIG. 1) for coupling the assembly 11 to the catheter 13 so that the user can withdraw the catheter 13 from a vessel, such as a vessel 16 in FIG. 2, by moving the assembly 11 in the direction of an arrow 17 in FIGS. 2 and 4, this being generally axially. In other words, the user grasps a portion of the assembly 11 and pulls on it in the direction of the arrow 17 to withdraw the catheter 13 from the vessel 16.

To accomplish this, the assembly 11 includes a body member 18. The body member 18 may take any of various shapes and sizes, such as the hollow tubular shape illustrated. It is composed of a generally rigid material, such as a thermoplastic material, and it extends along the longitudinal axis 14 from a proximal end 19 to a distal end 20, the passageway 12 extending along the longitudinal axis 14 through the distal end 20 (FIG. 1).

Various coupling arrangements may be utilized within the broader inventive concepts disclosed. The coupling components 15 of the illustrated assembly 11 are arranged in what is sometimes called a Touhy-Borst cap-and-compressible-disk arrangement. In this arrangement, an annular disk 21 of suitable elastomeric material such as silicone is disposed intermediate the distal end 20 of the body member 18 and a cap 21 that is dimensioned and arranged to be screwed onto the distal end 20.

When the cap 22 is screwed onto the distal end 20 as shown in FIG. 3, the disk 21 is compressed between the cap 22 and the distal end 20 so that the disk 21 deforms radially inwardly to bear against the catheter 13. This causes the disk 21 to engage the catheter 13 frictionally, with a force having a magnitude dependent on the degree to which the disk 21 is compressed, and this couples an axially-directed component of force from the body member 18 to the catheter 13 when the assembly 11 is moved in the direction of the arrow 17.

Screwing the cap 22 further onto the distal end 20 compresses the disk 21 all the more so that the disk 21 bears against the catheter 13 with more force to more securely grip the catheter 13. In this way, the coupling components 15 are adjustable to enable the user to select a desired maximum amount of force that can be coupled from the assembly 11 to the catheter 13.

The adjustment is made by screwing the cap 22 onto the distal end 20 until the catheter 13 is gripped with the desired force. The point at which this occurs may be determined by pulling on the catheter with a force just slightly greater than the desired maximum force. When the coupling components are properly adjusted, a force greater than the desired maximum force will cause the catheter 13 to slip through the disk 21. In other words, the catheter 13 and the assembly 11 slip longitudinally relative to each other if the maximum withdrawal force is exceeded.

According to another aspect of the invention, there is included means for providing a visually discernible indication of the relative magnitude of a force being coupled by the user to the assembly 11. This is accomplished in the device 10 with a handle member 23 that is dimensioned and arranged to be grasped by the user while fitting telescopingly within the body member 18.

The handle member 23 is moveably mounted, as illustrated, with a spring member 24, a nut member 25, and a guidepost member 26 in order to enable axial movement relative to the body member 18. The guidepost member 26 fits coaxially through the handle member 23 and it screws through the nut member 24 into the body member 18. Mounted in this way, the handle member 23 can slide along the guidepost member 26 while the spring member 24 couples it to the body member 18.

As the handle member 23 is pulled in the direction of the arrow 17 (FIG. 4), the spring member 24 elongates axially according to the force restraining the catheter 13 and the spring constant of the spring member 24 to provide an indication of the force applied to the body member 18. In other words, the handle member 23 is spring-coupled to the body member 18 to enable axial movement to a position indicative of the magnitude of a force being coupled from the handle member 23 to the body member 18.

A graduated scale 27 on the handle member 23 (FIGS. 2 and 4) cooperates with a pointer portion 28 (FIGS. 1, 2, and 4) formed by a cutout 29 in the proximal end 19 of the body member 18 (FIG. 1) to serve as means for indicating relative handle member position. The spring member 24 is suitable sized (two to three centimeters long, for example) and it is configured to have a suitable spring constant to cooperate with the graduated scale 27 (such as one hundred grams-per-inch, for example). With a spring constant of one hundred grams-per-inch and graduations spaced one-tenth inch (2.54 millimeters), each successive graduation represent an increase in force of ten grams.

The guidepost member 26 is screwed through the nut member 24 an amount that results in the graduated scale indicating zero when no force is applied to the spring member 24. This calibrates the device 10. As shown in FIGS. 1 and 5, the guidepost member 26 includes radially outwardly extending portions or stops 30 and 31 which fit in a star-shaped portion 33 of the passageway 12 that extends through the guidepost member 26. With the handle member 23 pushed axially toward the body member 18, the guidepost member 26 is screwed through the nut member 25 into the body member 18 as desired so that with the handle member 23 released (i.e., with no force applied to the handle member 23), the graduated scale 27 and pointer 28 indicate zero grams.

With the handle member 23 released, the stops 30 and 31 seat within the star-shaped portion 33 to engage the handle member 23 and thereby prevent the guidepost member 26 from turning from this calibrated position relative to the handle member 23, rotation of the handle member 23 being restricted by the spring member 24. This arrangement serves as means for retaining calibration.

In addition, the star-shaped portion 33 may be configured so that the stops 30 and 31 abut the interior of the handle member 23 before the handle member 23 can be pulled fully off of the guidepost member 26. As clearly depicted in FIG. 3, the stops 30 and 31 abut a shoulder portion 23A of the handle member 23. This arrangement serves as means for limiting axially movement of the handle member 23 relative to the body member 18 in order to limit the extension of the handle member 23.

Thus, the device 10 enables the user to continuously monitor the force exerted by the catheter 13 on the interior of the vessel 16. This may be caused, for example, by a balloon portion 35 of the catheter 13 as diagrammatically illustrated in FIG. 2, the balloon portion 35 bearing against an occlusion 36 as the catheter 13 is withdrawn from the vessel 16. The medical literature suggests that at shear forces under thirty grams, intimal damage is unlikely to occur. By setting the coupling components 15 at thirty grams so that the catheter 13 slips at forces greater than that, the user is provided with an additional safety factor.

To use the device 10, the catheter 13 is passed through the passageway 12 and secured using the coupling components 15 (i.e., the cap-and-compressible-disk arrangement). As the cap 22 is tightened, the disk 21 is compressed to reduce its inner diameter and thereby cause increasingly greater interference with the catheter 13. By holding the catheter 13 and pulling on the handle member 23, the user can adjust the cap 22 so that the catheter 13 slips at the desired force as indicated by the graduated scale 27 and the pointer 28.

Once the coupling components 15 are adjusted, the balloon portion 35 of the catheter 13 is advanced within the vessel 16 to a position distal of the occlusion 36. Then, the balloon portion 35 is inflated and the catheter 13 withdrawn by the user pulling on the handle member 23. This couples a withdrawal force from the user to the handle member 23, through the spring member 25 to the body member 18, and from there with the coupling components 15 to the catheter 13.

This force causes the spring member 25 to elongate accordingly so that the handle member 23 moves axially out of the body member 18 to a position indicative of the amount of force applied. This position is indicated by the graduated scale 27 and the pointer 28 to provide a visually discernible indication of the force applied.

With this force applied to the catheter 13 in the direction of the arrow 17 in FIG. 2, the catheter 13 is withdrawn from the vessel 16, unless and until the catheter 13 engages the vessel 16 sufficiently. This may occur by the balloon portion 35 bearing against the occlusion 36, and it may result in the user applying more force to the handle member 23. Of course, the graduated scale 27 and pointer 28 provide an indication of the greater force so that the user can directly limit the amount applied. However, if and when the force applied exceeds the maximum force for which the coupling components 15 are adjusted, the catheter 13 slips through the cap-and-compressible-disk arrangement so that the greater force is not exerted on the vessel 16.

Some bypass procedures use the internal mammary artery, and vessel spasm occurs once it is severed. The result is often a lack of continuous blood flow due to constriction. By dilating with a balloon-tipped catheter, flow can be restored, and monitoring of shear force in this application is extremely important as well.

Thus, this invention solves shear force problems by providing a device that can be attached to the proximal end of the catheter for the user to grip. The device couples only a desired maximum amount of force to the catheter so that vessel wall damage can be prevented, and it provides a visually discernible indication of the force being coupled, thereby achieving a greater safety factor.

As various changes may be made in the form, construction, and arrangement of the described components without departing from the spirit and scope of the invention and without sacrificing any of its advantages, all matter herein is to be interpreted as illustrative and not in any limiting sense.

What is claimed is:

1. A device for use in withdrawing a catheter from a vessel, comprising:
    an elongated body member extending along a longitudinal axis from a proximal end to a distal end, the body member defining a passageway through which to pass a catheter, the passageway extending along the longitudinal axis to an open distal end of the body member;
    means for coupling the body member to a catheter disposed within the passageway in order to enable a user to withdraw the catheter from a vessel by moving the body member axially, and for so coupling the body member to the catheter adjustably in order to enable the user to select a desired maximum amount of axially-directed force that can be coupled from the body member to the catheter;
    a handle member mounted on the body member, which handle member is dimensioned and arranged to be grasped by a user for purposes of applying an axially-directed force to the body member;
    means for coupling the handle member to the body member so that the handle member can move axially relative to the body member to a position indicative of the magnitude of an axially-directed force that the user applies with the handle member to the body member; and
    means for providing an indication of relative handle member position as an indication of the force applied to the body member;
    wherein the means for coupling the handle member to the body member includes:
    a guidepost member that fits coaxially through the handle member to threadingly engage the body member;
    the guidepost member having at least one radially outwardly extending portion;
    the handle member having a hollow interior through which the guidepost member fits; and
    the hollow interior having a star-shaped cross section dimensioned and arranged so that the radially outwardly extending portion engages the handle member to inhibit rotation of the guidepost member relative to the handle member.

2. A device as recited in claim 1, wherein:
    the coupling means has a maximum withdrawal force which it can transmit to the catheter to thereby limit the withdrawal force which the user can apply to the catheter and reduce the likelihood of injury; and
    the coupling means includes means for allowing the catheter and the assembly to slip longitudinally relative to each other if the maximum withdrawal force is exceeded.

3. A device as recited in claim 2, wherein:
    the maximum withdrawal force is adjustable.

4. A device as recited in claim 1, further comprising:
    a catheter having a portion that fits through the passageway.

5. A device as recited in claim 3, wherein the catheter includes:
    a balloon-type catheter.

6. A device as recited in claim 1, wherein the means for providing an indication of relative handle member position includes:
    a graduated scale disposed on the assembly in a position to indicate various handle member positions relative to the body member.

7. A device as recited in claim 6, wherein the means for coupling the body member to the catheter includes:
    a cap-and-compressible-disk arrangement.
    a cap-and-compressible-disk arrangement.

8. A device as recited in claim 6, wherein the means for coupling the handle member to the body member includes:
    a spring acting between the body member and the handle member.

9. A device as recited in claim 1, wherein the means for providing an indication of relative handle member position includes:
    a graduated scale attached to the handle member.

10. A device as recited in claim 6, wherein:

the body member and the handle member fit together telescopingly.

11. A device as recited in claim 6, further comprising: means for limiting axial movement of the handle member relative to the body member.

12. A device as recited in claim 11, wherein the means for limiting axial movement includes:
the handle member having an interior that is dimensioned and arranged so that the radially outwardly extending portion of the guidepost member abuts the handle member to limit axial movement of the handle member.

13. A device for use in withdrawing a catheter from a vessel, comprising:
an elongated body member extending along a longitudinal axis from a proximal end to a distal end, the body member defining a passageway through which to pass a catheter, the passageway extending along the longitudinal axis to an open distal end of the body member;
means for coupling the body member to a catheter disposed within the passageway in order to enable a user to withdraw the catheter from a vessel by moving the body member axially, and for so coupling the body member to the catheter adjustably in order to enable the user to select a desired maximum amount of axially-directed force that can be coupled from the body member to the catheter;
a handle member mounted on the body member, which handle member is dimensioned and arranged to be grasped by a user for purposes of applying an axially-directed force to the body member;
means for coupling the handle member to the body member so that the handle member can move axially relative to the body member to a position indicative of the magnitude of an axially-directed force that the user applies with the handle member to the body member; and
means for providing an indication of relative handle member position as an indication of the force applied to the body member;
wherein the means for coupling the handle member to the body member includes means for inhibiting rotational movement of the handle member relative to the body member.

14. A device as recited in claim 13 wherein the means for inhibiting rotational movement includes:
a guidepost member that fits coaxially through the handle member to threadingly engage the body member;
the guidepost member having at least one radially outwardly extending portion;
the handle member having a hollow interior through which the guidepost member fits; and
the hollow interior having a cross section dimensioned and arranged so that the radially outwardly extending portion engages the handle member to inhibit rotation of the handle member relative to the body member.

15. A device as recited in claim 13, wherein:
the body member and the handle member fit together telescopingly.

16. A device as recited in claim 15, wherein the means for coupling the handle member to the body member includes:
a spring connected to the body member and to the handle member.

17. A device for use in withdrawing a catheter from a vessel, comprising:
an elongated body member extending along a longitudinal axis from a proximal end to a distal end, the body member defining a passageway through which to pass a catheter, the passageway extending along the longitudinal axis to an open distal end of the body member;
means for coupling the body member to a catheter disposed within the passageway in order to enable a user to withdraw the catheter from a vessel by moving the body member axially, and for so coupling the body member to the catheter adjustably in order to enable the user to select a desired maximum amount of axially-directed force that can be coupled from the body member to the catheter;
a handle member mounted on the body member, which handle member is dimensioned and arranged to be grasped by a user for purposes of applying an axially-directed force to the body member;
means for coupling the handle member to the body member so that the handle member can move axially relative to the body member to a position indicative of the magnitude of an axially-directed force that the user applies with the handle member to the body member; and
means for providing an indication of relative handle member position as an indication of the force applied to the body member;
wherein the means for coupling the handle member to the body member includes means for limiting axial movement of the handle member relative to the body member.

18. A device as recited in claim 17, wherein the means for limiting axial movement includes:
a guidepost member that fits coaxially through the handle member to threadingly engage the body member, the guidepost member having at least one radially outwardly extending portion; and
the handle member having a hollow interior through which the guidepost member fits that is dimensioned and arranged so that the radially outwardly extending portion of the guidepost member abuts the handle member in order to limit axial movement of the handle member relative to the body member.

* * * * *

UNITED STATES PATENT AND TRADEMARK OFFICE
CERTIFICATE OF CORRECTION

PATENT NO. : 4,820,283

DATED : Apr. 11, 1989

INVENTOR(S) : David P. Schickling et al

It is certified that error appears in the above-identified patent and that said Letters Patent is hereby corrected as shown below:

Column 6, line 58 delete the second occurrence of "a cap-and-compressible-disk arrangement."

Signed and Sealed this

Ninth Day of January, 1990

Attest:

JEFFREY M. SAMUELS

Attesting Officer    Acting Commissioner of Patents and Trademarks